(12) United States Patent
Friess et al.

(10) Patent No.: US 9,090,700 B2
(45) Date of Patent: Jul. 28, 2015

(54) TUMOR THERAPY WITH AN ANTIBODY FOR VASCULAR ENDOTHELIAL GROWTH FACTOR AND AN ANTIBODY FOR HUMAN EPITHELIAL GROWTH FACTOR RECEPTOR TYPE 2

(75) Inventors: Thomas Friess, Diessen-Dettenhofen (DE); Max Hasmann, Munich (DE); Werner Scheuer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 452 days.

(21) Appl. No.: 12/947,264

(22) Filed: Nov. 16, 2010

(65) Prior Publication Data

US 2011/0064736 A1    Mar. 17, 2011

Related U.S. Application Data

(63) Continuation of application No. 11/725,777, filed on Mar. 20, 2007, now abandoned.

(30) Foreign Application Priority Data

Mar. 22, 2006   (EP) .................................... 06111523
Oct. 18, 2006   (EP) .................................... 06021815

(51) Int. Cl.
*A61K 39/395*    (2006.01)
*C07K 16/32*    (2006.01)
*C07K 16/22*    (2006.01)
*C07K 16/30*    (2006.01)
*A61K 39/00*    (2006.01)

(52) U.S. Cl.
CPC ................. *C07K 16/32* (2013.01); *C07K 16/22* (2013.01); *C07K 16/3015* (2013.01); *A61K 2039/507* (2013.01)

(58) Field of Classification Search
CPC .................. A61K 39/39558; A61K 2039/505; A61K 2039/507; A61K 47/48561; A61K 47/48569; A61K 51/1027; A61K 51/1045; C07K 2317/76; C07K 16/2863; C07K 16/22; C07K 16/28
See application file for complete search history.

(56) References Cited

U.S. PATENT DOCUMENTS

| 6,884,879 B1 | 4/2005 | Baca et al. |
| 2003/0190317 A1 | 10/2003 | Baca et al. |
| 2005/0112126 A1 | 5/2005 | Baca et al. |

FOREIGN PATENT DOCUMENTS

| EP | 0590058 B1 | 11/2003 |
| EP | 1 325 932 B1 | 4/2005 |
| EP | 1 579 871 | 9/2005 |
| WO | 92/22653 | 12/1992 |
| WO | 98/45331 | 10/1998 |
| WO | 00/69460 A1 | 11/2000 |
| WO | 01/00238 A1 | 1/2001 |
| WO | 01/00245 | 1/2001 |
| WO | 03/077841 | 9/2003 |
| WO | 03/087131 A2 | 10/2003 |
| WO | 2005/000900 A1 | 1/2005 |
| WO | 2005/012531 A2 | 2/2005 |
| WO | 2005/052005 A1 | 6/2005 |
| WO | 2005/063816 A2 | 7/2005 |
| WO | 2007/107329 A1 | 9/2007 |

OTHER PUBLICATIONS

Miller et al., "The Snark is a Boojum: the continuing problem of drug resistance in the antiangiogenic era" *Annals of Oncology* 14:20-28 ( 2003).
Pegram et al., "Phase I combined biological therapy of breast cancer using two humanized monoclonal antibodies directed against HER2 proto-oncogene and vascular endothelial growth factor (VEGF)" *Breast Cancer Research & Treatment* 88( SUPPL 1):S124-S125 ( 2004).
Walshe et al., "A Phase II Trial with Trastuzumab and Petruzumab in Patients with HER2-Overexpressed Locally Advanced and Metastatic Breast Cancer" *Clinical Breast Cancer* 6:535-539 ( 2006).
Sledge, "VEGF-Targeting Therapy for Breast Cancer" *J Mammary Gland Biol Neoplasia* 10:319-323 ( 2005).
Scheuer et al., "Enhanced antitumour effect by combination of HER2-targeting antibodies with bevacizumab in a human breast cancer xenograft model" *European Journal of Cancer* 4(12):66 (Nov. 1, 2006).
Pegram et al., "Combined Biological Therapy of Breast Cancer Using Monoclonal Antibodies Directed Against HER2/neu Protein and Vascular Endothelial Growth Factor" *Seminars in Oncology* 29(3 SUPPL 11):29-37 (Jun. 2002).
du Manoir et al., "Strategies for Delaying or Treating In vivo Acquired Resistance to Trastuzumab in Human Breast Cancer Xenografts" *Clinical Cancer Research* 12:904-916 ( 2006).
Herbst et al. et al., "Phase I/II Trial Evaluating the Anti-Vascular Endothelial Growth Factor Monoclonal Antibody Bevacizumab in Combination With the HER-1/Epidermal Growth Factor Receptor Tyrosine Kinase Inhibitor Erlotinib for Patients . . . " J Clin Oncol 23(11):2544-2555 (Apr. 10, 2005).
Rugo, "Bevacizumab in the Treatment of Breast Cancer: Rationale and Current Data" The Oncologist 9( SUPPL 1):43-49 ( 2004).
Marutaka et al., "A paclitaxel-resistant case of recurrent breast cancer responded to combination therapy of capecitabine and trastuzumab, Abstract" Gan To Kagaku Ryoho 32(12):2137-2139 (Dec. 2005).
FDA Commissioner announces Avastin Decision (Press Release FDA Nov. 18, 2011).
Epstein et al., "HER2-overexpressing human breast cancer xenografts exhibit increased angiogenic potential mediated by vascular endothelial growth factor (VEGF)" Breast Cancer Res Treat (Abstracts—Poster Session V), 76:S143 ( 2002).
Konecny et al. et al., "Association Between HER-2/neu and Vascular Endothelial Growth Factor Expression Predicts Clinical Outcome in Primary Breast Cancer Patients" Clin Cancer Res 10:1706-1716 (Mar. 1, 2004).

(Continued)

*Primary Examiner* — Hong Sang
(74) *Attorney, Agent, or Firm* — Cara M. Coburn

(57) ABSTRACT

The present invention provides a method of treating a breast cancer disease in a patient who has failed prior treatment with an anti-VEGF antibody, comprising administering to the patient a therapeutically effective amount of an anti-HER2 antibody while continuing said anti-VEGF antibody therapy. The invention also provides corresponding pharmaceutical kits and pharmaceutical compositions.

9 Claims, 1 Drawing Sheet

(56) References Cited

OTHER PUBLICATIONS

Decision of Rejection of the Japanese Patent Office and translation (Mar. 7, 2012).
Kurozumi, et al., The Journal of Saitama Medical University, vol. 28, No. 4, p. 184. Translated into English, 2001.
Bartsch et al., "Analysis of Trastuzumab and Chemotherapy in Advanced Breast Cancer After the Failure of at Least one Earlier Combination: An Observational Study" BMC Cancer 6(63) (2006).
Bengala et al., "Cardiac Toxicity of Trastuzumab in Metastatic Breast Cancer Patients Previously Treated with High-Dose Chemotherapy: A Retrospective Study" British Journal of Cancer 94:1016-1020 (2006).
Bernard Marty et al., "Monoclonal Antibody Based Targeted Therapy in Breast Cancer Current Status and Future Directions" Drugs 66(12):1577-1591 (2006).
Cobleigh et al., "A Phase I/II Dose-escalation Trial of Bevacizumab in Previously Treated Metastatic Breast Cancer" Seminars in Oncology 30(5):117-124 (2003).
Diaz-Rubio, "New Chemotherapeutic Advances in Pancreatic, Colorectal, and Gastric Cancers" The Oncologist 9(SUPPL 282-294) (2004).
"Evidence-Based Health Care" Bandolier 4(1) (1), 1997.
Fujiuchi et al., "Recent Perspectives Second-Line Chemotherapy for Breast Cancer" Gan to Kagaku Ryoho 32(1):11-4 (2005).
Kurebayashi et al., "Isolation and Characterization of a new Human Breast Cancer Cell Line, KPL-4, Expressing the Erb B Family Receptors and Interleukin-6" British Journal of Cancer 79(5-6):707-717 (1999).
Langmuir et al., Poster (Successful long-term Therapy with Bevacizumab (Avastin) in Solid Humors) pp. 1, 2002.
Miller et al., "Randomized Phase III Trail of Capecitabine Compared with Bevacizumab Plus Capecitabine in Patients with Previously treated Metastic Breast Cancer" Journal of Clinical Oncology 23(4):792-799 (2005).
Nahta et al., "In Vitro Effecs of Trastuzumab and Vinorelbine in Trastuzumab-Resistant" Cancer Chemother Pharmacol 53:186-190 (2004).
Nahta et al., "Mechanisms of Disease: Understanding Resistance to HER2-Targeted Therapy in Human Breast Cancer" Nature Clinical 3(5):269-280 (2006).
Ordonez et al., "Trastuzumab in Combination with Bevacizumab in Yes Advanced Breast Cancer Patient Resistant to Chemotherapy" Journal of Clinical Oncology 24(18S):10762 (2006).
Other Database, NCT00093535, (Phase I/II Combined Biological Therapy of Breast Cancer Using Monoclonal Antibodies Directed Against HER2/NEU Proto-Oncogene and Vascular Endothelial Growth Factor (VEGF)) Feb. 2, 2009.
Other Database, NCT00093535, (Phase I/II Study of Bevacizumab and Trastuzumab (Herceptin(R)) in Women with Relapsed or Metastatic HER2/neu-Overexpressing Adenocarcinoma of the Breast (Phase I Portion of Study Closed to Accrual as of Nov. 1, 2004)) Jun. 23, 2005.
Other Database, NCT02056587, (Everolimus in Patients with Metastic Renal Cell Carcinoma Following Progression on Prior Bevacizumab Treatment) Feb. 2014.
Pegram et al., "Phase II Combined Biological Therapy Targeting the HER2 Proto-Oncognene and the vascular Endothelial Growth Factor Using Trastuzumab (T) and Bevacizumab (B) as First Line Treatment of HER2-Amplified Breast Cancer." Breast Cancer Research Treatment(S28 SUPPL 1) (2006).
Pusztai et al., "Continued Use of Trastuzumab (Herceptin) After Progression on Trastuzumab Therapy in HER-2-Positive Metastatic Breast Cancer" Cancer Investigation :24:187191 (2006).
Rosen, "VEGF-Targeted Therapy: Therapeutic Potential and Recent Advances" The Oncologist 10:382-391 (2005).
Scheuer et al., Abstract (18th EORTC-NC-AACR Symposium on 'Molecular Targets and Cancer Therapeutice Prgue, Czech Republic, Nov. 7-10, 2006) pp. 1 (2006).
Steeg, "Tumor Metastasis: Mechanistic Insights and Clinical Challenges" Nature Medicine 12(8) (2006). .
Tomasevic et al., "Patterns of Relapse During Adjuvany Trastuzumab Therapy" Journal of Clinical Oncolgy 26(15S) (2008).
Translation of Decision of Rejection JPO, Application No. 2009-524943, pp. 3 (Jan. 9, 2013).
Untch et al., "Adjuvant Treatment with Trastuzumab in Patients with Breast Cancer" Dtsch Arztebl 103(50) (2006).
Valabrega et al., "Trastuzumab: Mechanism of Action, Resistance and Future Perspectives in HER2-Overexpressong Breast Cancer" Annais of Oncology 18:977-984 (2007).
Yeon et al., "Anti-erbB-2 Antibody Trastuzumab in the Treatment of HER2-Amplified Breast Cancer"Investigational New Drugs 23:391-09 (2005).
Garcia et al., "Sorafenib in Patients with Metastic Renal Cell Carcinoma Refractory to Either Sunitinib or Bevacizumab" Cancer 116:5383-5390 (Dec. 1, 2010).
Gill, "Evidence-Based Health Care" Bandolier 4(1):288 (Jan. 1997).
Hatake, "Molecular targeting drug" The Journl of Practical Pharmacy (Partial translation included), 56(4):1745-1749 (2005).
Rajer Renal Tumor "Changing Mechanisms of Action as a Strategy for Sequential targeted Therapy of Metastic Renal-Cell Carcinoma" (ISB: 978-953-51-0981-5 InTech DOI: 10.5772/55694), Prf. Jindong Chen (Ed.), InTech,:187-208 (2013).
Dummary of Clinical Trial www.clinicatrials.gov—Gov Identifier NCT02056587, Sponsor:Kidney Cancer Research Bureau (Feb. 2014).
Watanabe, "Trastuzumab (Herceptin)" Cancer Therapy and Host (Partial translation included), 17(4):351-360 (2005).

TUMOR THERAPY WITH AN ANTIBODY FOR VASCULAR ENDOTHELIAL GROWTH FACTOR AND AN ANTIBODY FOR HUMAN EPITHELIAL GROWTH FACTOR RECEPTOR TYPE 2

PRIORITY TO RELATED APPLICATIONS

This application is a continuation of U.S. application Ser. No. 11/725,777 filed Mar. 20, 2007, now abandoned, which claims benefit of European Application No. EP06111523.4, filed Mar. 22, 2006 and EP06021815.3, filed Oct. 18, 2006, all of which are incorporated herein by reference.

FIELD OF THE INVENTION

The present invention is directed to combined therapy with anti-HER2 and anti-VEGF antibodies. In particular, the invention concerns the use of such antibodies to treat breast cancer disease in a patient who has failed prior breast cancer treatment with an anti-VEGF antibody.

BACKGROUND OF THE INVENTION

Angiogenesis is implicated in the pathogenesis of a variety of disorders which include solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu. Rev. Physiol. 53 (1991) 217-239; and Garner, A, Vascular diseases, In: Pathobiology of ocular disease, A dynamic approach, (eds.) Garner and A, Klintworth, G K, 2nd Edition Marcel Dekker, New York, (1994), pp 1625-1710). In the case of solid tumors, the neovascularization allows the tumor cells to acquire a growth advantage and proliferative autonomy compared to the normal cells. Accordingly, a correlation has been observed between density of microvessels in tumor sections and patient survival in breast cancer as well as in several other tumors (Weidner, N., et al., N. Engl. J. Med. 324 (1991) 1-6; Horak, E. R., et al., Lancet 340 (1992) 1120-1124; and Macchiarini, P., et al., Lancet 340 (1992) 145-146).

Vascular endothelial growth factor (VEGF) is involved in the regulation of normal and abnormal angiogenesis and neovascularization associated with tumors and intraocular disorders (Ferrara, N., et al., Endocr. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer 73 (1996) 931-934; and Dvorak, H. F., et al., Am. J. Pathol. 146 (1995) 1029-1039). Anti-VEGF neutralizing antibodies suppress the growth of a variety of human tumor cell lines in mice (Kim, K. J., et al., Nature 362 (1993) 841-844; Warren, R. S., et al., J. Clin. Invest. 95 (1995) 1789-1797; Borgstrom, P., et al., Cancer Res. 56 (1996) 4032-4039; and Melnyk, O., et al., Cancer Res. 56 (1996) 921-924). WO 94/10202, WO 98/45332, WO 2005/00900 and WO00/35956 refer to antibodies against VEGF. Humanized monoclonal antibody bevacizumab (sold under the tradename Avastin®) is an anti-VEGF antibody used in tumor therapy and is the only anti-angiogenic agent approved for treatment of cancer (WO 98/45331).

HER2 is a member of the human epidermal growth factor receptor family and possesses protein kinase activity in its cytoplasmic domain. HER2 is over-expressed in tumor cells and is correlated with poor prognosis and survival. HER2 is therefore a valuable target of breast cancer therapy. Antibodies against HER2 are known from Takai, N., et al., Cancer 104 (2005) 2701-2708; Yeon, C. H., et al., Invest. New Drugs 23 (2005) 391-409; Wong, W. M., et al., Cancer Pract. 7 (1999) 48-50; Albanell, J., et al., Drugs Today (Barc). 35 (1999) 931-46.

Trastuzumab (sold under the tradename Herceptin®) is a recombinant humanized anti-HER2 monoclonal antibody used for the treatment of HER2 over-expressed/HER2 gene amplified metastatic breast cancer. Preclinical studies demonstrated that the antibody has anti-tumor activity in vivo and in vitro. Moreover, additive or synergistic enhancement of anti-tumor activity of trastuzumab was observed in combination with various anti-tumor agents in mouse models. In clinical studies, extension of survival was observed in HER2 overexpressing metastatic breast cancer patients.

According to WO 98/45331, the effectiveness of an anti-VEGF antibody in preventing or treating disease may be improved by administering the antibody serially or in combination with another agent that is effective for those purposes, such as an antibody capable of binding to HER2 receptor. WO 2005/012531 describes antibodies that may be combined with an anti-VEGF antibody (e.g. Avastin®) and/or anti-ErbB antibodies (e.g. Herceptin®) in the treatment of colorectal cancer, metastatic breast cancer and kidney cancer. According to WO 2005/063816, anti-VEGF antibodies may be combined with anti-ErbB antibodies in a treatment of metastatic breast cancer. WO 2005/00090 and WO 2003/077841 also disclose the combination of anti-VEGF antibodies with anti-ErbB2 antibodies for tumor therapy.

Clinical oncologists are in agreement that the failure of cancer treatment is not necessarily caused by the growth of the primary tumor, which is generally dealt with using surgery, but rather by the metastatic spread into different organs. The regression of primary tumors by different cytotoxic drugs is not always indicative for anti-metastatic activity per se. On the contrary, enhanced metastasis has been observed in response to several anti-cancer drugs (Geldof, A. A., et al., Anticancer Res. 8 (1988) 1335-1339; Murphy, S. B., J. Clin. Oncol. 11 (1993) 199-201; and De Larco, J. E., et al., Cancer Res. 61 (2001) 2857-2861). Clearly there exists a need to develop treatment therapies that target not only the primary tumor, but also suppress metastasis.

SUMMARY OF THE INVENTION

The invention comprises the use of an anti-HER2 antibody and an anti-VEGF antibody for the manufacture of a medicament for treating a breast cancer disease in a patient who has failed prior cancer therapy with an anti-VEGF antibody, comprising administering to the patient a therapeutically effective amount of an anti-HER2 antibody and an anti-VEGF antibody.

In a preferred embodiment, the invention comprises the use of trastuzumab and bevacizumab for the manufacture of a medicament for treating a breast cancer disease characterized by an overexpression of the HER2 receptor protein in a patient who has failed prior therapy with an anti-VEGF antibody such as bevacizumab, comprising administering to the patient a therapeutically effective amount of trastuzumab and bevacizumab.

The invention further comprises a method of treating a breast cancer disease in a patient who has failed prior therapy with an anti-VEGF antibody, comprising administering to the patient a therapeutically effective amount of an anti-HER2 antibody while continuing said anti-VEGF antibody therapy.

The invention further comprises a method of treating a breast cancer disease, in a patient who has failed prior therapy with an anti-VEGF antibody, comprising administering to the patient a therapeutically effective amount of trastuzumab while continuing bevacizumab therapy, wherein the breast cancer disease is characterized by an overexpression of the HER2 receptor protein.

The invention further comprises a method for increasing the duration of survival of a patient having breast cancer disease who has failed prior therapy with an anti-VEGF antibody, comprising administering to the patient effective amounts of an anti-VEGF antibody and an anti-HER2 antibody, whereby the co-administration of the anti-VEGF antibody and the anti-HER2 antibody effectively increases the duration of survival.

The invention further comprises a method for increasing the progression free survival of a patient having breast cancer disease who has failed prior therapy with an anti-VEGF antibody, comprising administering to the patient effective amounts of an anti-VEGF antibody and an anti-HER2 antibody, whereby the co-administration of the anti-VEGF antibody and the anti-HER2 antibody effectively increases the duration of progression free survival.

The invention further comprises a method for treating a group of patients, having breast cancer disease and having failed prior therapy with an anti-VEGF antibody, comprising administering to the patient effective amounts of an anti-VEGF antibody and an anti-HER2 antibody, whereby the co-administration of the anti-VEGF antibody and the anti-HER2 antibody effectively increases the response rate in the group of patients.

The invention further comprises a method for increasing the duration of response of a patient having breast cancer disease who has failed prior therapy with an anti-VEGF antibody, comprising administering to the patient effective amounts of an anti-VEGF antibody and an anti-HER2 antibody, whereby the co-administration of the anti-VEGF antibody and the anti-HER2 antibody effectively increases the duration of response.

The invention further comprises a method of treating a patient having breast cancer disease who has failed prior therapy with an anti-VEGF antibody, comprising administering to the patient effective amounts of an anti-VEGF antibody and an anti-HER2 antibody, whereby the co-administration of the anti-VEGF antibody and the anti-HER2 antibody results in statistically significant and clinically meaningful improvement of the treated patient as measured by the duration of survival, progression free survival, response rate or duration of response.

This invention further comprises a method for reducing metastasis in a patient having breast cancer disease who has failed prior therapy with an anti-VEGF antibody, comprising administering to the patient effective amounts of an anti-VEGF antibody and an anti-HER2 antibody, whereby the co-administration of the anti-VEGF antibody and the anti-HER2 antibody effectively reduces metastasis.

The invention further comprises a method for treating a group of patients, having breast cancer disease and having failed prior therapy, with an anti-VEGF antibody, comprising administering to the patient effective amounts of an anti-VEGF antibody and an anti-HER2 antibody, whereby the co-administration of the anti-VEGF antibody and the anti-HER2 antibody effectively reduces metastasis in the group of patients.

The invention provides an article of manufacture (e.g., pharmaceutical kit) comprising one or more containers, and preferably at least two containers, a pharmaceutical composition within a first container comprising an anti-VEGF antibody, a pharmaceutical composition within a second container comprising an anti-HER2 antibody and a package insert instructing the user of the composition to administer to a patient, having breast cancer disease who has failed prior therapy with an anti-VEGF antibody, the anti-VEGF antibody within said first container and an anti-HER2 antibody within said second container.

The invention further provides for a pharmaceutical composition comprising an anti-HER2 antibody and an anti-VEGF antibody useful in the treatment of breast cancer disease in a patient which has failed prior therapy with an anti-VEGF antibody. Preferably the anti-HER2 antibody is trastuzumab. Also preferably the anti-VEGF antibody is bevacizumab.

DETAILED DESCRIPTION OF THE INVENTION

Figure 1:
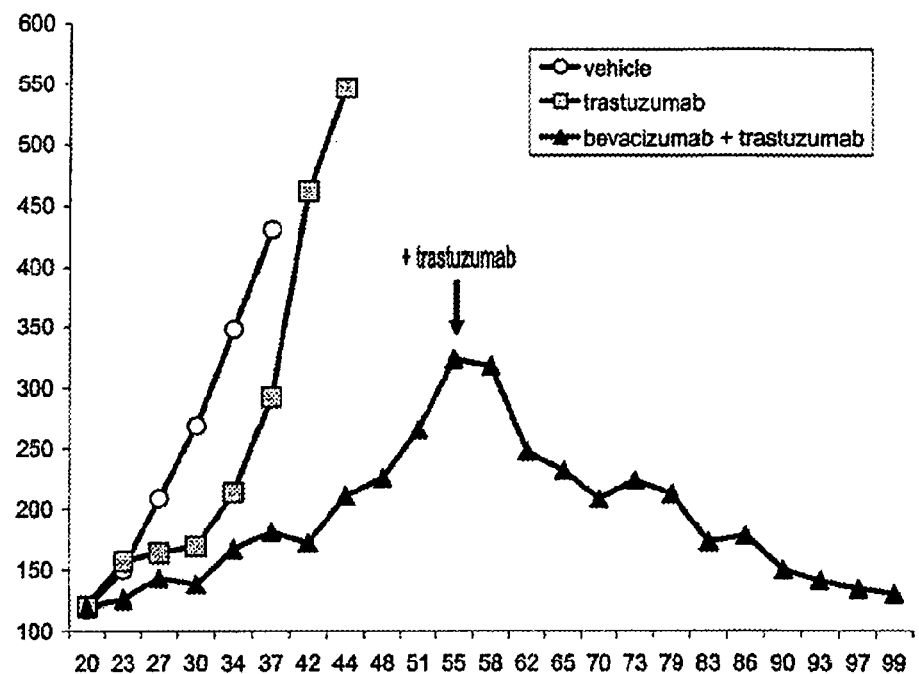
FIG. 1 Antitumor activity of combined trastuzumab and bevacizumab treatment on tumor growth after bevacizumab treatment failure. Mean values of tumor volume ($mm^3$) plotted on the y-axis; number of days after injection of tumor cells plotted on the x-axis. Vehicle (circles), trastuzumab at loading dose of 30 mg/kg and maintenance dose of 15 mg/kg (squares), bevacizumab at 5 mg/kg until day 55 when treatment, also includes trastuzumab at 15 mg/kg (triangles).

All references cited herein are hereby incorporated by reference in their entirety.

Definitions

The term "VEGF" according to the invention refers to the vascular endothelial cell growth factor (Swiss-Prot No. P 15692), alternative splicing forms (see e.g. Leung, D. W., et al., Science, 246 (1989) 1306-1309; and Houck, K. A., et al., Mol. Endocrin. 5 (1991) 1806-1814) and active fragments, preferably N-terminal fragments thereof.

The term "anti-VEGF antibody" according to the invention is an antibody that binds specifically to VEGF. The preferred humanized anti-VEGF antibody or variant anti-VEGF antibody herein binds human VEGF with a Kd value of no more than about $1 \times 10^{-8}$M and preferably no more than about $5 \times 10^{-9}$M. Preferably the anti-VEGF antibody is a monoclonal antibody that binds to the same epitope as recombinant humanized anti-VEGF monoclonal antibody generated according to Presta, L. G., et al., Cancer Res. 57 (1997) 4593-4599. A preferred antibody is bevacizumab. Anti-VEGF antibodies and methods for their manufacture are e.g. described in U.S. Pat. No. 6,054,297, US 2003/0190317, U.S. Pat. Nos. 6,632,926, 6,884,879, and US 2005/0112126.

Bevacizumab comprises mutated human IgG1 framework regions and antigen-binding complementarity-determining regions from a murine anti-hVEGF monoclonal antibody that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 Daltons and is glycosylated. Bevacizumab and its method of preparation are described in EP 1 325 932.

HER2 is a 185-kDa growth factor receptor also referred to as neu and c-erbB-2 (Slamon, D. J., et al., Science 235 (1987) 177-182; Swiss-Prot P04626) whose function is related to neoplastic transformation in human breast cancer cells. Overexpression of this protein has been identified in 20-30% of breast cancer patients where it correlates with regionally advanced disease, increased probability of tumor recurrence, and reduced patient survival. As many as 30-40% of patients having gastric, endometrial, salivary gland, non-small cell lung, pancreatic, ovarian, peritoneal, prostate, or colorectal cancers may also exhibit overexpression of this protein. Anti-HER2 antibodies and methods for their manufacture are e.g. described in U.S. Pat. No. 6,054,297, WO 89/06692, U.S. Pat. Nos. 6,953,842, 6,949,245, 6,399,063, 6,165,464, 6,054,297, 5,772,997, WO 2003/087131, WO 01/00245, WO 01/00238, WO 00/69460, WO 00/52054, WO 99/31140 and WO 98/17797. In a preferred embodiment of the invention, the anti-HER2 antibody is trastuzumab. Trastuzumab and its method of preparation are described in EP 0 590 058.

The term "overexpression" of the HER2 receptor protein is intended to indicate an abnormal level of expression of the HER2 receptor protein in a cell from a tumor within a specific tissue or organ of the patient relative to the level of expression in a normal cell from that tissue or organ. Patients having a cancer characterized by overexpression of the HER2 receptor can be determined by standard assays known in the art. Preferably overexpression is measured in fixed cells of frozen or paraffin-embedded tissue sections using immunohistochemical (IHC) detection. When coupled with histological staining, localization of the targeted protein can be determined and extent of its expression within a tumor can be measured both qualitatively and semi-quantitatively. Such IHC detection assays are known in the art and include the Clinical Trial Assay (CTA), the commercially available LabCorp 4D5 test, and the commercially available DAKO HercepTest® (DAKO, Carpinteria, Calif.). The latter assay uses a specific range of 0 to 3+ cell staining (0 being normal expression, 3+ indicating the strongest positive expression) to identify cancers having overexpression of the HER2 protein (see the Herceptin® (trastuzumab) full prescribing information, September 1998, Genentech Inc., San Francisco, Calif.). Thus, patients having a cancer characterized by overexpression of the HER2 protein in the range of 1+, 2+, or 3+, preferably 2+ or 3+, more preferably 3+ would benefit from the methods of therapy of the present invention.

The term "breast cancer disease" refers to the uncontrolled growth of abnormal breast cells. It includes ductal carcinoma in situ, invasive ductal carcinoma, lobular carcinoma in situ, invasive lobular carcinoma, medullary carcinoma, Paget's disease of the nipple and metastatic breast cancer, as well as other cancer diseases of the breast as known to one of ordinary skill in the art.

The term "failed prior therapy with an anti-VEGF antibody" or "treatment failure" as used herein refers to tumor patients who failed to respond to previous therapy with an anti-VEGF antibody ("non-responders") or who initially responded to previous therapy, but in whom the therapeutic response was not maintained (referred to as "relapsers"). Preferably the term "failed prior therapy with an anti-VEGF antibody" refers to relapsers. Treatment failure (respectively Response (RE) and Non-Response (NR)) is established based on the medical judgment of a practitioner ascertained by the results from clinical and laboratory data that are generally known in the art to assess patient treatment. Such data may be obtained, by way of example, from clinical examination, cytological and histological techniques, endoscopy and laparoscopy, ultrasound, CT, PET and MRI scans, chest X-ray and mammography, and measuring the concentration of tumor markers, such as CEA, Cyfra, CA15-3, interleukin 8 and soluble HER2. In this context "treatment failure" is defined as the absence of clinical improvement. Alternatively, RECIST criteria may be used to determine tumor response (Therasse, P., et al., J. Nat. Cancer Institute 92 (2000) 205-216) In this context "treatment failure" is defined as either "incomplete response/stable disease" or "progressive disease".

According to these RECIST criteria, tumor response for solid tumors (Therasse, P., et al., J. Nat. Cancer Institute 92 (2000) 205-216) is categorized in dependency of the volume progression or regression of the tumors (e.g. measured via CT) into four levels: complete response (CR) or partial response (PR), stable disease (SD) and progressive disease (PD) (see Table 1). Furthermore the European Organization for Research and Treatment of Cancer (EORTC) proposed a categorization into four levels in dependency of the metabolism of the tumors measured via 2-[$^{18}$F]-Fluoro-2-deoxyglucose positron emission tomography (FDG-PET) (Young H., et al., Eur. J. Cancer 35 (1999) 1773-1782 and Kellof, G. J., et al., Clin. Cancer Res. 11 (2005) 2785-2808): complete metabolic response (CMR) or partial metabolic response (PMR), stable metabolic disease (SMD) and progressive metabolic disease (PMD) (see Table 2).

TABLE 1

CT-Criteria (acc. to RECIST)

| CT-measurement: Change in sums longest diameters | RECIST |
|---|---|
| Disappearance; conformed at 4 weeks (after treatment start) | CR |
| 30% decrease; confirmed at 4 weeks | PR |
| Neither PR nor PD criteria met | SD |
| 20% increase, no CR, PR, SD documented before increased disease | PD |

TABLE 2

Proposed FDG-PET criteria (acc. to EORTC, see Young H., et al., Eur J Canc 35 (1999) 1773-1782)

| PET-measurement | Proposed FDG-PET criteria |
|---|---|
| Complete resolution of 2-[$^{18}$F]-Fluoro-2-deoxy-glucose (FDG) tumor uptake | CMR |
| Reduction of a minimum of 15-25% of standardized uptake value (SUV) after one treatment cycle, and of >25% after more than one treatment cycle | PMR |
| Increase of standardized uptake value (SUV) <25% or decrease of SUV <15% No visible increase the extent of FDG tumor uptake | SMD |

TABLE 2-continued

Proposed FDG-PET criteria
(acc. to EORTC, see Young H., et al.,
Eur J Canc 35 (1999) 1773-1782)

| PET-measurement | Proposed FDG-PET criteria |
|---|---|
| Increase of SUV >25%<br>Visible increase of FDG tumor uptake (>20% of longest dimension)<br>Appearance of new FDG uptake in metastatic lesions | PMD |

Thus, preferably, "Response (RE)" and "Non-Response (NR)" according to this invention are established based on data acquired by the combination of computer tomography (CT) and 2-[$^{18}$F]-Fluoro-2-deoxyglucose positron emission tomography (FDG-PET) (Kellof, G. J., et al., Clin. Cancer Res. 11 (2005) 2785-2808, and Young H., et al., Eur. J. Canc. 35 (1999) 1773-1782) using both the RECIST and FDG-PET criteria described above. Accordingly Response (RE) and Non-Response (NR) according to this invention are determined preferably as follows:

Response (RE): CR or PR is established via CT-RECIST criteria (Table 1) and at the same time CMR or PMR is established via FDG-PET (Table 2). Thus Response (RE) means one of the following four cases for combined CT and PET measurement: CR and CMR, PR and PMR, CR and PMR, and PR and CMR.

Non-Response (NR): SD or PD is established via CT-RECIST criteria (Table 1) and at the same time SMD or PMD is established via FDG-PET (Table 2). Thus the following four cases for combined CT and PET measurement signify Non-Response (NR): SD and SMD, SD and PMD, PD and SMD, and PD and PMD.

Usually the response is determined at around 3 to 8 weeks, preferably at around 6 weeks, after treatment start. This response determination is usually repeated at intervals of 4 to 8 weeks, preferably of 6 to 8 weeks. When at the first determination a significant response (RE) was identified, then a relapse (that means a Non-Response (RE) after the first determination) can be determined at earliest at the second response determination.

In this context, the term "patient who has failed prior therapy with an anti-VEGF antibody" refers to a patient, in whom either at the first response determination Non-Response (NR) is established ("Non-Responder") or at the first response determination Response (RE) is established, and in the second or a subsequent response determination Non-Response (NR) is established ("Relapser").

The term "metastasis" according to the invention refers to the transmission of cancerous cells from the primary tumor to one or more sites elsewhere in a patient causing secondary tumors. A tumor formed by cells that have spread is called a "metastatic tumor" or a "metastasis". The metastatic tumor contains cells that are like those in the original (primary) tumor. Means to determine if a cancer has metastasized are known in the art and include tumor marker tests, bone scan, chest X-ray, computed tomography (CT), computerized axial tomography (CAT), molecular resonance imaging (MRI), positron emission tomography (PET), single photon emission computed tomography (SPECT), fluorescence imaging (FI), and bioluminescent imaging (BLI) and tumor marker tests (see e.g. Helms, M. W., et al., Contributions to microbiology 13 (2006) 209-231, and Pantel, K., et al., J. Nat. Cancer Inst. 91 (1999) 1113-1124).

As used herein, the term "patient" preferably refers to a human in need of treatment to treat cancer, or a precancerous condition or lesion. However, the term "patient" can also refer to non-human animals, preferably mammals such as dogs, cats, horses, cows, pigs, sheep and non-human primates, among others, that are in need of treatment.

The term "group" refers to a group of patients as well as a sub-group of patients.

The term "package insert" refers to instructions customarily included in commercial packages of therapeutic products, which may include information about the indications, usage, dosage, administration, contraindications and/or warnings concerning the use of such therapeutic products.

The cancer may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or urethra, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions. In a preferred embodiment, the cancer to be treated is a breast cancer disease. Also in a preferred embodiment, the cancer is characterized by an overexpression of the HER2 receptor protein.

Detailed Description

The invention provides a combined therapy method of treating a breast cancer disease, comprising administering to the patient a therapeutically effective amount of an anti-HER2 antibody and an anti-VEGF antibody wherein the breast cancer disease is characterized by an overexpression of the HER2 receptor protein. More specifically, the invention provides a method of treating a breast cancer disease in a patient who has failed prior therapy with an anti-VEGF antibody, comprising administering to the patient a therapeutically effective amount of an anti-HER2 antibody and an anti-VEGF antibody wherein preferably the anti-VEGF antibody is bevacizumab, the patient is human; the anti-HER2 antibody is trastuzumab, and wherein preferably the breast cancer disease is characterized by an overexpression of the HER2 receptor protein.

The invention further comprises a method of treating a breast cancer disease in a patient who has failed prior therapy with an anti-VEGF antibody, comprising administering to the patient a therapeutically effective amount of an anti-HER2 antibody while continuing said anti-VEGF antibody therapy.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed an overall beneficial course of action.

The term "patient" as used herein means a mammal, preferably a human.

The term "therapeutically effective amount" or "effective amount" means the amount of the subject compound or combination that will elicit the biological or medical response of a tissue, system, animal or human that is being sought by the researcher, veterinarian, medical doctor or other clinician.

The invention further comprises the use of an anti-HER2 antibody and an anti-VEGF antibody for the manufacture of a medicament for treating a breast cancer disease in a patient who has failed prior therapy with an anti-VEGF antibody, comprising administering to the patient a therapeutically effective amount of an anti-HER2 antibody while continuing said anti-VEGF antibody therapy. The antibodies may be administered separately or simultaneously.

The term "method for manufacturing a medicament" relates to the manufacturing of a medicament for use in the indication as specified herein and in particular for use in the treatment of tumors, tumor metastases, or cancer in general. The term relates to the so-called "Swiss-type" claim format in the indication specified.

In the context of this invention, additional other cytotoxic, chemotherapeutic or anti-cancer agents, or compounds that enhance the effects of such agents may be used in the anti-VEGF antibody plus anti-HER2 antibody combination. Such agents include, for example: alkylating agents or agents with an alkylating action, such as cyclophosphamide (CTX; e.g. Cytoxan®), chlorambucil (CHL; e.g. Leukeran®), cisplatin (CisP; e.g. Platinol®) busulfan (e.g. Myleran®), melphalan, carmustine (BCNU), streptozotocin, triethylenemelamine (TEM), mitomycin C, and the like; anti-metabolites, such as methotrexate (MTX), etoposide (VP16; e.g. Vepesid®), 6-mercaptopurine (6MP), 6-thioguanine (6TG), cytarabine (Ara-C), 5-fluorouracil (5-FU), capecitabine (e.g. Xeloda®), dacarbazine (DTIC), and the like; antibiotics, such as actinomycin D, doxorubicin (DXR; e.g. Adriamycin®), daunorubicin (daunomycin), bleomycin, mithramycin and the like; alkaloids, such as vinca alkaloids such as vincristine (VCR), vinblastine, and the like; and other antitumor agents, such as paclitaxel (e.g. Taxol®) and pactitaxel derivatives, the cytostatic agents, glucocorticoids such as dexamethasone (DEX; e.g. Decadron®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: arnifostine (e.g. Ethyol®), dactinomycin, mechlorethamine (nitrogen mustard), streptozocin, cyclophosphamide, lomustine (CCNU), doxorubicin lipo (e.g. Doxil®), gemcitabine (e.g. Gemzar®), daunorubicin lipo (e.g. Daunoxome®), procarbazine, mitomycin, docetaxel (e.g. Taxotere®), aldesleukin, carboplatin, oxaliplatin, cladribine, camptothecin, CPT 11 (irinotecan), 10-hydroxy 7-ethylcamptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

In the context of this invention, an anti-hormonal agent may be used in the anti-VEGF antibody plus anti-HER2 antibody combination. As used herein, the term "anti-hormonal agent" includes natural or synthetic organic or peptidic compounds that act to regulate or inhibit hormone action on tumors. Antihormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. Fareston®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as Zoladex® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N-6-(3-pyridinylcarbonyl)-L-lysyl-N6-(3-pyridinylcarbonyl)-D-lysyl-L-leucyl-N-6-(1-methylethyl)-L-lysyl-L-proline (e.g Antide®, Ares-Serono); the LHRH antagonist ganirelix acetate; the steroidal anti-androgens cyproterone acetate (CPA) and megestrol acetate, commercially available as Megace® (Bristol-Myers Oncology); the nonsteroidal anti-androgen flutamide (2-methyl-N-[4, 20-nitro-3-(trifluoromethyl)phenylpropanamide), commercially available as Eulexin® (Schering Corp.); the nonsteroidal anti-androgen nilutamide, (5,5-dimethyl-3-[4-nitro-3-(trifluoromethyl-4'-nitrophenyl)-4,4-dimethyl-imidazolidine-dione); and antagonists for other nonpermissive receptors, such as antagonists for RAR (retinoic acid receptor), RXR (retinoid X receptor), TR (thyroid receptor), VDR (vitamin-D receptor), and the like.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

In the context of this invention, additional antiproliferative agents may be used in the anti-VEGF antibody plus anti-HER2 antibody combination, including, for example: Inhibitors of the enzyme farnesyl protein transferase and inhibitors of the receptor tyrosine kinase PDGFR, including the compounds disclosed and claimed in U.S. Pat. Nos. 6,080,769; 6,194,438; 6,258,824; 6,586,447; 6,071,935; 6,495,564; 6,150,377; 6,596,735 and 6,479,513, and International Publication WO 01/40217.

In the context of this invention, an effective amount of ionizing radiation may be carried out and/or a radiopharmaceutical may be used in addition to the anti-VEGF antibody plus anti-HER2 antibody combination. The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the EGFR kinase inhibitor according to this invention is an antibody, it is also possible to label the antibody with such radioactive isotopes.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in International Publication WO 99/60023.

The antibodies are administered to a patient according to known methods, by intravenous administration as a bolus or by continuous infusion over a period of time, by intramuscular, intraperitoneal, intracerobrospinal, subcutaneous, intra-articular, intrasynovial, or intrathecal routes. Intravenous or subcutaneous administration of the antibodies is preferred.

The amount of anti-VEGF and anti-HER2 antibody administration and the timing of administration will depend on the type (species, gender, age, weight, etc.) and condition of the patient being treated and the severity of the disease or condition being treated.

Dosages for administration of the antibodies according to the invention are about 1 µg/kg to 50 mg/kg (e.g. 0.1-20 mg/kg) of antibody by one or more separate administrations, or by continuous infusion. A typical daily dosage might range from about 1 µg/kg to about 100 mg/kg. In a preferred aspect, the antibodies are administered every two to three weeks, at a dose ranged from about 1 mg/kg to about 15 mg/kg. A preferred dose for bevacizumab is 5 mg/kg once every 14 days as an IV infusion until disease progression is detected. A preferred dose for trastuzumab is a loading dose of 4 mg/kg administered over a 90-minute period and subsequent weekly infusions of 2 mg/kg administered over a 30-minute period.

The present invention further provides a kit (pharmaceutical kit) comprising an anti-VEGF antibody (preferably a pharmaceutical composition thereof), an anti-HE2 antibody (preferably a pharmaceutical composition thereof) and a package insert instructing the user of said compositions to administer to a patient, having breast cancer disease who has failed prior therapy with an anti-VEGF antibody, the anti-VEGF antibody, preferably within pharmaceutical composition and the anti-HER2 antibody, preferably within a pharmaceutical composition. In a preferred embodiment, the kit containers may further include a pharmaceutically acceptable carrier. The kit may further include a sterile diluent, which is preferably stored in a separate additional container. The kit may further include a package insert comprising printed instructions directing the use of the combined treatment as a method for a breast cancer disease. Preferably, the pharmaceutical kit will include a first container storing a pharmaceutical composition comprising an anti-VEGF antibody and a second container storing a pharmaceutical composition comprising an anti-HER2 antibody.

Alternatively, the present invention also provides a pharmaceutical kit comprising a pharmaceutical composition comprising an anti-VEGF antibody, a pharmaceutical composition comprising an anti-HE2 antibody, and a package insert instructing the user of said compositions to administer to a patient having breast cancer disease, who has failed prior therapy with an anti-VEGF antibody, said anti-VEGF antibody pharmaceutical composition and an anti-HER2 antibody pharmaceutical composition, wherein the anti-VEGF antibody pharmaceutical composition and the anti-HER2 antibody pharmaceutical composition are packaged either in a single container or in two separate containers.

The present invention further provides a pharmaceutical composition, in particular for use in treating a breast cancer disease that has failed prior therapy with anti-VEGF antibody, comprising an anti-HER2 antibody and an anti-VEGF antibody. Such composition optionally comprises pharmaceutically acceptable carriers and/or excipients, such as those commonly known to one of ordinary skill in the art. In a preferred embodiment the anti-VEGF antibody is bevacizumab and the anti-HER2 antibody is trastuzumab. The present invention also provides a pharmaceutical kit comprising said pharmaceutical composition comprising said anti-HER2 antibody and said anti-VEGF antibody.

The following Experimental details are provided to aid the understanding of the present invention, the true scope of which is set forth in the appended claims. It is understood that the specific methods and results discussed are merely illustrative of the invention and are not to be considered in any way limited thereto.

Introduction

The current study examined the antitumor activity of the combination of bevacizumab and trastuzumab after the failure of bevacizumab treatment alone in human breast xenograft model. Further aims of the study were to examine the effects of treatment on metastasis.

Test Agents

Trastuzumab was provided as a 25 mg/ml stock solution in Histidine-HCl, alpha-alpha Trehalose (60 mM), 0.01% Polysorb, pH 6.0 (Herceptin®). Bevacizumab was provided as a 25 mg/ml stock solution in Na-phosphate, alpha-alpha Trehalose (60 mM), 0.01% Polysorb, pH 6.0 (Avastin®). Both solutions were diluted appropriately in PBS for injections.

Cell Lines and Culture Conditions

The human breast cancer cell line KPL-4 has been established from the malignant pleural effusion of a breast cancer patient with an inflammatory skin metastasis and overexpresses ErbB family receptors. (Kurebayashi, J., et al., Br. J. Cancer 79 (1999) 707-17) Tumor cells are routinely cultured in DMEM medium (PAA Laboratories, Austria) supplemented with 10% fetal bovine serum (PAA) and 2 mM L-glutamine (Gibco) at 37° C. in a water-saturated atmosphere at 5% $CO_2$. Culture passage is performed with trypsin/EDTA 1×(PAA) splitting twice/week. Cell passage P6 was used for in vivo study.

Animals

SCID beige (C.B.-17) mice; age 10-12 weeks; body weight 18-20 g (Charles River, Sulzfeld, Germany) are maintained under specific-pathogen-free condition with daily cycles of 12 h light/12 h darkness according to international guidelines (GV-Solas; Felasa; TierschG). After arrival, animals are housed in the quarantine part of the animal facility for one week to get accustomed to new environment and for observation. Continuous health monitoring is carried out on regular basis. Diet food (Alltromin) and water (acidified pH 2.5-3) are provided ad libitum.

Tumor Growth Inhibition Studies In Vivo

Tumor cells were harvested (trypsin-EDTA) from culture flasks (Greiner TriFlask) and transferred into 50 ml culture medium, washed once and resuspended in PBS. After an additional washing step with PBS and filtration (cell strainer; Falcon 100 μm) the final cell titer was adjusted to $0.75 \times 10^8$/ml. Tumor cell suspension was carefully mixed with transfer pipette to avoid cell aggregation. Anesthesia was performed using a Stephens inhalation unit for small animals with pre-incubation chamber (plexiglas), individual mouse nose-mask (silicon) and Isoflurane (Pharmacia-Upjohn, Germany) in a closed circulation system. Two days before injection the fur of the animals was shaved. For intra mammary fat pad (i.f.m.p.) injection, cells were injected orthotopically at a volume of 20 μl into the right penultimate inguinal mammary fat pad of each anesthetized mouse. For the orthotopic implantation, the cell suspension was injected through the skin under the nipple. Tumor cell injection corresponds to day 1 of the experiment.

Monitoring

Animals were controlled daily for detection of clinical symptoms of adverse effects. For monitoring throughout the experiment, the body weight of the animals was documented two times weekly and the tumor volume was measured by caliper twice weekly. Primary tumor volume was calculated according to NCI protocol (TW=1/2ab2, where a and b are long and short diameters of tumor size in mm, Teicher, B., Anticancer drug development guide, Humana Press 5 (1997) 92). Calculation values were documented as mean and standard deviation.

Treatment of Animals

Tumor-bearing mice were randomized when the tumor volume was roughly 100 mm³ (n=10 for each group). Each group was closely matched before treatment, which began 20 days after tumor cell injection. Vehicle group (group 1) received 10 ml/kg PBS buffer intraperitoneally (i.p.) once weekly. Trastuzumab (group 2) was administered i.p. at a loading dose of 30 mg/kg, followed by once weekly doses of 15 mg/kg (maintenance dose). The anti-VEGF antibody bevacizumab was given i.p. at a dosage of 5 mg/kg twice weekly (group 3). At day 40, treatment for group 3 was switched to a combination treatment of bevacizumab (5 mg/kg twice weekly i.p.) with trastuzumab (15 mg/kg once weekly i.p.).

Evaluation of Metastasis

Spread of tumor cells into the lung was determined in sacrificed animals. Metastasis was measured according to Schneider, T., et al., Clin. Exp. Metastasis 19 (2002) 571-582. Briefly, lung tissue was harvested and human Mu sequences were quantified by real-time PCR. Higher human DNA levels, quantified by real-time PCR, correspond to higher levels of metastasis.

Results

The effect of treatment on primary tumor growth is shown in FIG. 1 and Table 3. Tumors in the vehicle group (group 1) grew rapidly and mice were sacrificed 38 days after injection of tumor cells because of ulceration of tumors and the development of clinical symptoms. Monotherapy with trastuzumab (group 2) exerted no significant effect on tumor volume and mice were therefore sacrificed at day 44. Treatment with bevacizumab suppressed tumor growth significantly; however, tumors started to regrow around day 44. Combination treatment of bevacizumab and trastuzumab beginning at day 55 resulted in complete inhibition of tumor growth during the duration of the experiment (day 99) and treatment was well tolerated.

TABLE 3

Antitumor activity of combined trastuzumab and bevacizumab treatment on tumor growth after bevacizumab treatment failure (data for FIG. 1). Mean tumor volume in mm³ is reported and the standard deviation (SD).

| Day | Vehicle | SD | trastuzumab | SD | trastuzumab + bevacizumab | SD |
|---|---|---|---|---|---|---|
| 20 | 118 | 31 | 120 | 31 | 119 | 35 |
| 23 | 150 | 30 | 157 | 57 | 126 | 44 |
| 27 | 209 | 51 | 164 | 77 | 143 | 67 |
| 30 | 269 | 76 | 169 | 82 | 138 | 65 |
| 34 | 348 | 114 | 214 | 114 | 167 | 76 |
| 37 | 431 | 138 | 293 | 162 | 181 | 78 |
| 42 | | | 462 | 275 | 172 | 63 |
| 44 | | | 547 | 315 | 211 | 65 |
| 48 | | | | | 226 | 68 |
| 51 | | | | | 266 | 78 |
| 55 | | | | | 324 | 103 |
| 58 | | | | | 318 | 100 |
| 62 | | | | | 248 | 81 |
| 65 | | | | | 232 | 75 |
| 70 | | | | | 209 | 69 |
| 73 | | | | | 224 | 56 |
| 79 | | | | | 213 | 68 |
| 83 | | | | | 173 | 57 |
| 86 | | | | | 178 | 80 |
| 90 | | | | | 150 | 73 |
| 93 | | | | | 141 | 74 |
| 97 | | | | | 134 | 67 |
| 99 | | | | | 130 | 76 |

Figure 2:
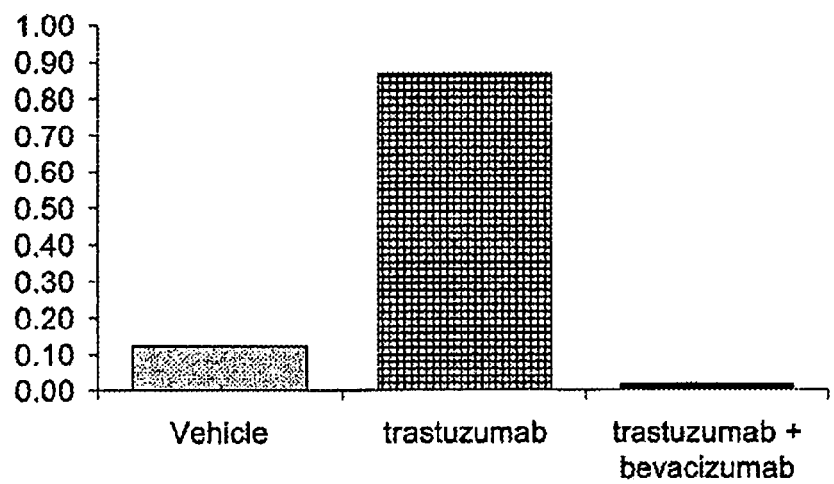
FIG. 2 Effect of combined trastuzumab and bevacizumab treatment on lung metastasis. Mean value of human Alu DNA sequence (ng/ml) quantitated from lung tissue using real-time PCR and plotted on the y-axis.

The effect of treatment on lung metastasis is shown in FIG. 2 and Table 4. The combination of trastuzumab and bevacizumab after bevacizumab treatment failure resulted in a sharp decrease in metastasis. Levels of human Alu sequences (correlating to invasion of tumor cells into secondary tissue) are significantly lower in animals treated with combination therapy at 99 days over vehicle treated animals that were sacrificed at 28 days and over trastuzumab treated animals sacrificed on day 44. This surprising effect on metastasis is in contrast with the effect seen with other cytotoxic drugs (Geldof, A. A., et al., Anticancer Res. 8 (1988) 1335-1339; Murphy, J. Clin. Oncol. 11 (1993) 199-201, and De Larco, J. E., et al., Cancer Res. 61 (2001) 2857-2861).

TABLE 4

Effect of treatment on lung metastasis. Alu DNA was quantified by real-time PCR and is reported for each animal.

|  | Vehicle | trastuzumab | trastuzumab + bevacizumab |
|---|---|---|---|
| human DNA | 0.224 | 1.609 | 0.010 |
| [ng/ml] | 0.225 | 0.084 | 0.010 |
|  | 0.148 | 0.586 | 0.014 |
|  | 0.011 | 0.055 | 0.009 |
|  | 0.037 | 2.919 | 0.012 |
|  | 0.058 | 0.078 | 0.010 |
|  | 0.084 | 2.741 | 0.041 |
|  | 0.099 | 0.017 | 0.010 |
|  | 0.048 | 0.340 | 0.016 |
|  | 0.279 | 0.232 | 0.027 |
| mean | 0.1212* | 0.8661** | 0.098 |
| median | 0.0915 | 0.2861 | 0.088 |

Statistical significance of combination treatment
*p = 0.001
**p = <0.001

The invention claimed is:

1. A combined therapy method of treating a breast cancer disease in a patient who has failed prior therapy with an anti-VEGF antibody, comprising administering to the patient a therapeutically effective amount of an anti-HER2 antibody and an anti-VEGF antibody, wherein the breast cancer disease is characterized by an overexpression of the HER2 receptor protein, and wherein said method demonstrates tumor regression.

2. The method of claim 1, wherein the patient is human.

3. The method of claim 2, wherein the anti-VEGF antibody is bevacizumab.

4. The method of claim 2 wherein the anti-HER2 antibody is trastuzurmab.

5. A method of reducing metastasis of a breast cancer that was non-responsive to prior therapy with an anti-VEGF antibody in a patient, comprising administering to the patient effective amounts of an anti-VEGF antibody and an anti-HER2 antibody, whereby the co-administration of the anti-VEGF antibody and the anti-HER2 antibody effectively reduces metastasis, as quantified by real-time PCR, and wherein the cancer is characterized by an overexpression of the HER2 receptor protein.

6. The method of claim 5, wherein the patient is human.

7. The method of claim 6, wherein the anti-VEGF antibody is bevacizumab.

8. The method of claim 6, wherein the anti-HER2 antibody is trastuzumab.

9. The method of claim 5, wherein the reduction of metastasis is in lung metastasis.

* * * * *